(12) United States Patent
Matsunaga

(10) Patent No.: US 6,706,760 B2
(45) Date of Patent: Mar. 16, 2004

(54) WASP CONTROLLING AGENT

(75) Inventor: Tadahiro Matsunaga, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/013,473

(22) Filed: Dec. 13, 2001

(65) Prior Publication Data
US 2002/0085979 A1 Jul. 4, 2002

Related U.S. Application Data

(62) Division of application No. 09/260,605, filed on Mar. 2, 1999, now abandoned.

(30) Foreign Application Priority Data

Mar. 20, 1998 (JP) ............................................. 10-071888

(51) Int. Cl.⁷ ........................ A01N 25/02; A01N 25/06; A01N 53/00
(52) U.S. Cl. ........................ 514/531; 424/405; 424/45; 424/8; 424/195.1; 514/691; 514/572
(58) Field of Search ................................. 424/409, 407, 424/45, 8, 195.1; 514/783, 691, 572, 531

(56) References Cited

U.S. PATENT DOCUMENTS

| 4,067,990 A | | 1/1978 | Dulat et al. |
| 4,234,567 A | * | 11/1980 | Flanner |
| 4,295,581 A | * | 10/1981 | Yamaguchi et al. |
| 5,091,183 A | * | 2/1992 | Yano et al. |
| 5,872,143 A | * | 2/1999 | Tanaka et al. |
| 6,114,384 A | | 9/2000 | Bessette et al. |

FOREIGN PATENT DOCUMENTS

| JP | B22560417 | 9/1996 |

* cited by examiner

Primary Examiner—Edward J. Webman
(74) Attorney, Agent, or Firm—Birch, Stewart, Kolasch & Birch, LLP

(57) ABSTRACT

A wasp controlling liquid formulation, which comprises a pesticidal compound as an active ingredient and at least 30% by weight of a saturated hydrocarbon that has a boiling point from 90° C. to 200° C., provides superior potency and an ability to knock down or kill wasps before the wasp has a chance to formidably sting someone.

2 Claims, No Drawings

WASP CONTROLLING AGENT

This application is a divisional of co-pending application Ser. No. 09/260,605, filed on Mar. 2, 1999, now abandoned, the entire contents of which are hereby incorporated by reference and for which priority is claimed under 35 U.S.C. § 120; and this application claims priority of Application No. 10-071888 filed in Japan on Mar. 20, 1998 under 35 U.S.C. § 119.

The present invention relates to a wasp controlling agent that has the ability to quickly kill or knock down wasps, and more particularly to a wasp controlling agent that comprises a pesticidal ingredient and a saturated hydrocarbon which has a boiling point from about 90° C. to 200° C.

BACKGROUND OF THE INVENTION

Wasps are winged Hymenoptera insects that usually possess a more or less formidable sting. The wasp sting is known to usually have a painful effect on humans, and various wasp stings have been known to cause death under certain unfortunate conditions. In each wasp stinging case, a controlling agent that quickly kills or knocks down wasps would have been helpful.

A wasp repellent comprising 2-methyl-4-oxo-3-(2-propynyl)cyclopent-2-enyl chrysanthemate, described in Japanese patent No. 2560417, may be utilized to control a minimal quantity of wasps, but is not sufficient to control a multiplicity of wasps in cases such as controlling wasp housings. A wasp controlling agent that has expeditious activation would control a larger amount of wasps in a shorter amount of time and would be more sufficient, in view of decreasing the possibility of a wasp sting.

SUMMARY OF THE INVENTION

The objective of the present invention is to serve as a wasp controlling agent with surprisingly expeditious efficiency. The efficiency of the wasp controlling agent has superior potency and provides the wasp controlling agent an ability to knock down or kill wasps before the wasp has a chance to formidably sting someone.

Accordingly, the wasp controlling agent of the present invention comprises a pesticidal ingredient and a saturated hydrocarbon that has a boiling point from about 90° C. to 200° C. More particularly, the wasp controlling agent comprises 30% by weight or more of said saturated hydrocarbon when the wasp controlling agent is a liquid formulation. When the wasp controlling agent comprises a propellant, the wasp controlling agent essentially consists of at least one propellant and the above mentioned wasp controlling liquid formulation.

DETAILED DESCRIPTION OF THE INVENTION

The wasp controlling agent of the present invention as a liquid formulation usually comprises a pesticidal ingredient, a saturated hydrocarbon with a boiling point from about 90° C. to 200° C., and when necessary, the wasp controlling agent may optionally comprise a solvent, spreading agent, synergist, propellant and/or deodorant. More particularly, the wasp controlling agent comprises from about 0.0005% to 5% by weight of the pesticidal ingredient, preferably from about 0.1% to 3% of said pesticidal ingredient, and about 30% by weight or more of the saturated carbon, preferably from 30% to 99.95% by weight of said saturated hydrocarbon, even more preferably from 40% to 99.9% by weight of said saturated hydrocarbon. When the wasp controlling agent comprises a propellant, the amount of the saturated hydrocarbon and pesticidal ingredient is calculated from a weight that has the weight of the propellant excluded from the weight of the wasp controlling agent. Therefore, the wasp controlling agent comprising a propellant comprises the saturated hydrocarbon at an adjusted percentage of about 30% by weight or more and the pesticidal ingredient at an adjusted percentage from about 0.0005% to 5% by weight. The amount of the propellant is also adjusted to the weight of the wasp controlling agent that excludes the weight of the propellant, and consequently, the wasp repelling agent usually comprises from about 5% to 250% by adjusted weight of propellant, preferably 10% to 70% by adjusted weight. Aerosol formulations wherein the wasp controlling agent comprises a propellant, liquid formulations wherein the propellant is excluded, and mixtures of formulations thereof are possible formulations of the wasp controlling agent.

The pesticidal ingredient of the present invention may be, for example, pyrethroid compounds such as prallethrin, imiprothrin, phthalthrin, allethrin, transfluthrin, resmethrin, phenothrin, cyphenothrin, permethrin, cypermethrine, ethofenprox, cyfluthrine, deltamethrine, bifenthrine, fenvalerate, fenpropathrine and (S)-2-methyl-4-oxo-3-(2-propynyl)-cyclopent-2-enyl (1R)-trans-3-(2,2-dichlorovinyl)-2,2-dimethylcyclopropanecarboxylate; organophosphorus compounds such as dichlorvos; and carbamate compounds; and mixtures thereof. It is preferable to utilize active pyrethroid compounds such as prallethrin, imiprothrin, phthalthrin, allethrin, transfluthrin, and (S)-2-methyl-4-oxo-3-(2-propynyl)-cyclopent-2-enyl (1R)-trans-3-(2,2-dichlorovinyl)-2,2dimethylcyclopropanecarboxylate, or active organic phosphor compounds such as dichlorvos. It is more preferable to utilize active pyrethroid compounds such as prallethrin, imiprothrin and (S)-2-methyl-4-oxo-3-(2-propynyl)-cyclopent-2-enyl (1R)-trans-3-(2,2-dichlorovinyl)-2,2-dimethylcyclopropanecarboxylate; and even more preferable to utilize prallethrin or (S)-2-methyl-4-oxo-3-(2-propynyl)-cyclopent-2-enyl (1R)-trans-3-(2,2-dichlorovinyl)-2,2-dimethylcyclopropanecarboxylate. Usually, the pesticidal ingredient comprises about 50% by weight or more of said active pyrethroid compounds or said active organophosphorus compounds, and preferably comprises 60% by weight or more of said active pyrethroid compounds or said active organophosphorus compounds. It is usually preferable to mix said active pyrethroid compounds or said active organophosphorus compounds with phenothrin, cyphenothrin, permethrin, cypermethrin, ethofenprox, cyfluthrin, deltamethrin, bifenthrine, fenvalerate or fenprpathrin to reinforce the activity against wasps.

Paraffin or naphthene hydrocarbons with a boiling point of about 90° C. to 200° C. are suitable examples of the saturated hydrocarbon, and more particularly, n-pentane, 2-methylhexane, 3-methylhexane, 3-ethylpentane, n-octane, 2-methylheptane, 3-methylheptane, 4-methylheptane, 3-ethylhexane, 2,2dimethylhexane, 2,4-dimethylhexane, 2,5-dimethylhexane, 3,3-dimethylhexane, 3,4-dimethylhexane, 2-methyl-3-ethylpentane, 2,2,3-trimethylpentane, 2,2,4-trimethylpentane, 2,3,3-trimethylpentane, 2,3,4-trimethylpentane, 2,2,3,3-tetramethylpentane, n-nonane, 2-methyloctane, 3-methyloctane, 4-methyloctane, 2,4-dimethylheptane, 2,5-dimethylheptane, 2,6dimethylheptane, 2,2,5-trimethylhexane, 2,3,5-trimethylhexane, 3,3-diethylpentane, n-decane, 2-methylnonane, 3-methylnonane, 4-methylnonane, 5-methylnonane, 2,4-dimethyloctane, 2,5-dimethyloctane, 2,6-dimethyloctane, 2,7-dimethyloctane, 3,6-dimethyloctane, 4-n-propylheptane, 2,2,6-trimethylheptane, 2,4,6-trimethylheptane, 3,3,5-trimethylheptane. 3,4-diethylhexane, 2,2,3,4-tetramethylhexane, 3,3,4,4-tetramethylhexane, n-undecane, ethylcyclopentane, methylcyclohexane, 1,1 dimethylcyclohexane, 1,2-dimethylcyclohexane 1,3-dimethylcyclohexane, 1,4-dimethylcyclohexane. ethylcyclohexane, cyclooctane, isopropylcyclohexane, n-propylcyclohexane, 1,2,4-trimethylcyclohexane, n-butylcyclohexane and t-butylcyclohexane, or a mixture thereof are suitable saturated hydrocarbons. Examples of purchasable paraffin or naphthene hydrocarbons that may be utilized as the saturated hydrocarbon include Isopar H, Isopar G, Isopar E, Isopar C, Exxol D-30, Exxol D-40 (the previous, products of Exxon Chemicals), Nisseki Isozol 300 and Nisseki Naphthazol L (the previous, products of Nihon Sekiyu Kagaku Company).

As the propellant, nitrogen gas; pressurized gases such as pressurized air and carbonate gas; hydrofluorocarbons such as HFC-152a and HFC-134a; liquified gases such as dimethylether; liquified petroleum gases such as propane, butane and isobutane; and mixtures thereof are suitable propellants that may be utilized for the present invention.

The wasp controlling agent may comprise additional solvents, for example, alcohols such as isopropyl alcohol, ethyl alcohol, oleyl alcohol and lauryl alcohol; aromatic hydrocarbons such as alkylbenzene; non-saturated hydrocarbons such as octane; glycols such as low molecular weight polyethylene glycol and low molecular weight polypropylene glycol; ethers such as alkylphenyl ether; and chlorine solvents dichloromethane, but is not limited to thereto, since other solvents are also known to improve the solubility of the pesticidal ingredient.

The wasp controlling agent may also optionally comprise a spreading agent such as lanolin to improve the attachment of the present invention to wasps or wasp housings. The wasp controlling agent may comprise a deodorant, for example, natural essential oils such as lavender oil, or synthetic fragrances such as geraniol to reduce the smell of the present wasp controlling agent.

In order to intensify the activity of the pesticidal ingredient, for example, synergists such as piperonylbutoxide, N-octylbicycloheptanedicarboxyimide (MGK-264), 1,1'-oxybis(2,3,3,3-tetrachloropropane) (S421) maybe optionally added. The amount of the synergist is dependent upon the pesticidal ingredient, and is usually 10 or less parts by weight of the pesticidal ingredient, preferably 5 or less parts by weight.

The liquid formulation or aerosol formulation may be utilized on wasps or wasp housings. For example, said aerosol formulation may be obtained by mixing the liquid formulation and the propellant within a pressure resistant container, and the nozzle that is usually adjoined to the pressure resistant container may be utilized to directly spray the wasps or wasp housings. The pressure within the pressure resistant container is usually 4 to 9 kg/cm$^2$ at 25° C., but may differ upon the desired spraying distance of the present invention and/or the sort of propellant incorporated to the formulation. A liquid formulation may be produced by mixing the pesticidal ingredient, the saturated hydrocarbon and, when necessary, solvents, the optional ingredients and so on mentioned previously.

The liquid formulation may be utilized in machine powered sprayers and sprayers which employ a pressurized gas dispersal device and vaporizer that utilizes a heating device.

Examples of wasps which are controlled by the present invention include Vespidae such as yellow hornet (*Vespa simillima*), *Vespa analis, Vespa mandarinia, Vespa crabro, Vespula vulgaris, Vespula austriaca* and *Dolichovespula media* as well as Polistes spp. such as long-legged wasp (*Polistes hebraeus*), yellow long-legged wasp (*Polistes snelleni*), *Polistes nimpha, Polistes associus*, and so on.

Hereinafter, the examples explain the present invention more specifically, but do not limit the present invention.

EXAMPLES

Example 1

An oil formulation was prepared by dissolving 2.33 g of prallethrin (purity 93%) and 1.17 g of permethrin (93%) in paraffinic hydrocarbon (product name: Isopar-G: C9/2%, C10/73%, C11/25%, Exxon Chemical Company; boiling point given in table 1) to make the complete body 750 g (about 1L). An aerosol composition comprising 0.6 g of prallethrin and 0.3 g of permethrin per 215 g (about 300 mL) was then produced by packing 194 g of the obtained oil formulation, attaching a valve to the aerosol can, sealing said aerosol can, packing 21 g (42 mL) of LPG by use of the valve stem (gage pressure 7.2 kg/cm$^2$, 20° C.), and then formulating with nitrogen gas (negligible parts by weight) until the inner pressure of the product was 6.0±0.4 kg/cm$^2$ at 25° C.

Example 2

An oil formulation was prepared by dissolving 1.17 g of fenvalerate as well as 2.33 g of a 52:48 mixture of imiprothrin and isopropyl myristate in 290 g of isopropyl alcohol and then paraffinic hydrocarbon (product name: isopar-G: C9/2%, C10/73%, C11/25%, Exxon Chemical Company; boiling point given in table 1) to make the complete body 760 g (about 1L). An aerosol composition comprising 0.6 g of imiprothrin and 0.3 g of fenvalerate per 217 g (about 300 mL) was then produced by packing 196 g (about 258 mL) of the obtained oil formulation, attaching a valve to the aerosol can, sealing said aerosol can, packing 21 g (42 mL) of LPG by use of the valve stem (gage pressure 7.2 kg/cm$^2$, 20° C.), and then formulating with nitrogen gas (negligible parts by weight) until the inner pressure of the product was 6.0±0.4 kg/cm$^2$ at 25° C.

Example 3

Liquid formulations were produced by dissolving 0.32 parts by weight of prallethrin in a solvent to make the complete body 100 parts by weight. The utilized solvents are given in the following table.

TABLE 1

| Formulation name | Solvent | boiling points of the solvents (° C.) | | | | |
|---|---|---|---|---|---|---|
| | | initial | 5% | 50% | 95% | end |
| formulation #1 | Isopar G (Exxon Chemical Company; paraffinic hydrocarbon: C9/2%, C10/73%, C11/25%) | 158 | 159 | 161 | 172 | 175 |
| comparative formulation #1 | Neothiozol (Chuo Kasei Company; paraffinic hydrocarbon) | 200 min. | 215 min (10%) | 220 min. | 280 max. | — |
| comparative formulation #2 | Kerosene | 210 | — | 238 | — | 283 |
| comparative formulation #3 | Alkylbenze DA/DA-4 (Sumitomo Chemical Company; alkylbenzene) | — | 228 | 295 | 305 | — |
| comparative formulation #4 | Isopropanol (Kansai Kagaku Company) | boiling point: 82.5° C. | | | | |

Subsequently, adult *Vespa analis* Fabricius that were captured from a natural setting were anesthetized with carbonate gas. Three (3) *Vespa analis* Fabricius were grouped into to transparent resin cups (diameter 12 cm, height 10 cm), and had a nylon net cover the top of each cup to prevent escape. After the *Vespa analis* Fabricius recovered from the anesthetization, 2 mL of the liquid formulation was sprayed, by use of a pressurized sprayer, onto each group of *Vespa analis* Fabricus from 20 cm above said cup. The number of *Vespa analis* Fabricius knocked down and lost their liveliness were examined after each determined amount of time. The results are given in table 2.

TABLE 2

| examined oil sample | examined bee amount | knocked down *Vespa analis* Fabricius after spraying | | | | | | | | |
|---|---|---|---|---|---|---|---|---|---|---|
| | | 10 sec. | 20 sec. | 30 sec. | 40 sec. | 50 sec. | 60 sec. | 80 sec. | 100 sec. | 120 sec. |
| Example 1 | 3 | 1 | 3 | | | | | | | |
| comparative example 1 | 3 | 1 | 1 | 3 | | | | | | |
| comparative example 2 | 3 | 0 | 1 | 2 | 3 | | | | | |
| comparative example 3 | 3 | 0 | 0 | 0 | 2 | 2 | 2 | 3 | | |
| comparative example 4 | 3 | 0 | 0 | 0 | 0 | 0 | 0 | 1 | 1 | 1 |

Example 4

One liter (1L) liquid formulations were produced by dissolving 2.50 g of prallethrin (purity 93%) or 4.48 g of a 52:48 mixture of imiprothrin and isopropyl myristate in a solvent described in table 3. Two hundred fifty-eight milliliters (258 mL) of the obtained liquid formulation was packed into an aerosol container. The aerosol container had a valve attached, was then sealed, and had 21 g of LPG packed through the valvestem until the gage pressure was 7.2 kg/cm$^2$ at 20° C. In addition, nitrogen gas was packed until the inner pressure of the product was 6.0±0.4 kg/cm$^2$ at 25° C., to prepare 300 mL of an aerosol formulation. Variables of each formulation are given in the following table.

TABLE 3

| Formulation Name | Active Ingredient | Solvent | Concentration of active ingredient |
|---|---|---|---|
| formulation #2 | Prallethrin | Isopar G | 0.6 g/215 g |
| formulation #3 | Imiprothrin | 1. 290 g isopropanol<br>2. Isopar G | 0.6 g/215 g |
| formulation #4 | Imiprothrin | 1. 440 g isopropyl myristic acid<br>2. Isopar G | 0.6/228 g |

TABLE 3-continued

| Formulation Name | Active Ingredient | Solvent | Concentration of active ingredient |
|---|---|---|---|
| comparative formulation #5 | Imiprothrin | Alkylbenzene DA/DA-40 | 0.6 g/244 g |

Note: the imiprothrin mixture in formulation #3 and #4 was dissolved in isopropanol or isopropyl myristic acid before utilizing Isopar G.

Adult *Vespa xanathoptera* Cameron that were captured from a natural setting were anesthetized with carbonate gas. Five (5) *Vespa xanathoptera* Cameron were grouped into netted nylon cages (diameter 8 cm, height 20 cm). After the *Vespa xanathoptera* Cameron recovered from anesthetization, a reinforcement was prepared to hang the cage 1.2 m above ground level. The *Vespa xanathoptera* Cameron were sprayed for 2 to 3 seconds through the cage, from a position 2 m outside of the cage, with the aerosols. The *Vespa xanathoptera* Cameron knocked down and completely stopped moving, including the convulsions of the legs, were considered dead, and were examined after each determined amount of time. The results are given table 4.

TABLE 4

| Experiment number | Observation | Dead and knock downed insects after spraying | | |
|---|---|---|---|---|
| | | 5 sec | 10 sec | 15 sec |
| example 2 | amount knocked down | 5 | | |
| | amount dead | | | |
| example 3 | amount knocked down | 5 | | |
| | amount dead | 0 | 5 | |
| example 4 | amount knocked down | 5 | | |
| | amount dead | 0 | 5 | |
| comparative example 5 | amount knocked down | 3 | 5 | |
| | amount dead | 0 | 0 | 5 |

Example 5

Two samples of 1L liquid formulations were produced by dissolving 2.43 g of (S)-2-methyl-4-oxo-3-(2-propynyl)-cyclopent-2-enyl (1R)-trans-3-(2,2-dichlorovinyl)-2,2-d in a an appropriate solvent. Formulation #5 utilized Isopar G and comparative formulation #6 utilized Neothiozol as the solvent. Two hundred fifty-eight milliliters (258 mL) of the obtained liquid formulation was packed into an aerosol can. The aerosol container had a valve attached, was then sealed, and had 21 g of LPG packed through the valvestem until the gage pressure was 7.2 kg/cm$^2$ at 20° C. In addition, nitrogen gas was packed until the inner pressure of the product was 6.0±0.4 kg/cm$^2$ at 25° C. to prepare 300 mL of an aerosol formulation.

Adult *Vespa mandarinia* Smith that were captured from a natural setting were anesthetized with carbonate gas. Five (5) adult *Vespa mandarina* Smith were grouped into to each transparent resin cup (diameter 12 cm, height 10 cm), and had a nylon net cover the top of each cup to prevent escape. After the *Vespa mandarinia* Smith recovered from anesthetization, 2 mL of the aerosol formulation was sprayed onto each group of *Vespa mandarinia* Smith from 20 cm above the said cup. After spraying, the *Vespa mandarinia* Smith knocked down and lost their liveliness were examined after each determined amount of seconds. The results are given in Table 5.

TABLE 5

| Formulation | Knocked down insects after spraying | | |
|---|---|---|---|
| | 10 sec. | 20 sec. | 30 sec. |
| Formulation #5 | 0 | 5 | |
| Comparative formulation #6 | 0 | 2 | 5 |

What is claimed is:

1. A method of controlling wasps, said method comprising:

applying to the wasp or a habitat of the wasp, a wasp controlling composition consisting essentially of (i) a liquid formulation of 0.005% to 5% by weight of the pyrethroid compound and 30% to 99.95% by weight of the saturated hydrocarbon that has boiling point from 90° C. to 200° C.; and (ii) a propellant.

2. A method of controlling wasps, said method comprising:

applying to the wasp or a habitat of the wasp, a wasp controlling composition consisting essentially of (i) a liquid formulation of 0.1% to 3% by weight of the pyrethroid compound and 40% to 99.9% by weight of the saturated hydrocarbon that has boiling point from 90° C. to 2000° C.; and (ii) a propellant.

* * * * *